United States Patent [19]
Zamierowski

[11] Patent Number: 5,261,893
[45] Date of Patent: * Nov. 16, 1993

[54] FASTENING SYSTEM AND METHOD

[76] Inventor: David S. Zamierowski, 8500 Reinhardt, Leawood, Kans. 66206

[*] Notice: The portion of the term of this patent subsequent to Nov. 13, 2007 has been disclaimed.

[21] Appl. No.: 699,936

[22] Filed: May 14, 1991

Related U.S. Application Data

[63] Continuation-in-part of Ser. No. 504,598, Apr. 3, 1990, Pat. No. 5,100,396, which is a continuation-in-part of Ser. No. 332,699, Apr. 3, 1989, Pat. No. 4,969,880.

[51] Int. Cl.$^5$ .............................................. A61M 5/32
[52] U.S. Cl. .................................. 604/180; 604/280; 604/305; 128/DIG. 26
[58] Field of Search .......................... 604/174–176, 604/179, 180, 304, 305, 307, 313, 26, 49, 332, 280; 128/DIG. 26, 155, 156

[56] References Cited

U.S. PATENT DOCUMENTS

| | | | |
|---|---|---|---|
| 1,355,846 | 10/1920 | Rannells | 604/305 |
| 2,547,758 | 4/1951 | Keeling | |
| 2,969,057 | 10/1961 | Simmons | 604/307 |
| 3,367,332 | 2/1968 | Groves | |
| 3,682,180 | 8/1972 | McFarlane | |
| 3,826,254 | 7/1974 | Mellor | 604/180 |
| 4,080,970 | 3/1978 | Miller | |
| 4,165,748 | 8/1979 | Johnson | |
| 4,261,363 | 4/1981 | Russo | |
| 4,275,721 | 6/1981 | Olson | |
| 4,297,995 | 11/1981 | Golub | 604/308 |
| 4,333,468 | 6/1982 | Geist | |
| 4,373,519 | 2/1983 | Errede et al. | |
| 4,382,441 | 5/1983 | Svedman | |
| 4,392,853 | 7/1983 | Muto | |
| 4,419,097 | 12/1983 | Rowland | |
| 4,475,909 | 10/1984 | Eisenberg | |
| 4,480,638 | 11/1984 | Schmid | |
| 4,525,166 | 6/1985 | Leclerc | |
| 4,540,412 | 9/1985 | Van Overloop | |
| 4,543,100 | 9/1985 | Brodsky | |
| 4,569,348 | 2/1986 | Hasslinger | |
| 4,605,399 | 8/1986 | Weston et al. | 604/305 |
| 4,608,041 | 8/1986 | Nielsen | |
| 4,640,688 | 2/1987 | Hauser | |
| 4,743,232 | 5/1988 | Kruger | 604/307 |
| 4,838,883 | 6/1989 | Matsuura | |
| 4,840,187 | 6/1989 | Brazier | |
| 4,863,449 | 9/1989 | Thirriault et al. | |
| 4,878,901 | 11/1989 | Sachse | |
| 4,897,081 | 1/1990 | Poirier et al. | |
| 4,906,233 | 3/1990 | Moriuchi et al. | 604/174 |
| 4,919,654 | 4/1990 | Kalt | |
| 4,941,882 | 7/1990 | Ward et al. | 604/305 |
| 4,953,565 | 9/1990 | Tachibana et al. | 604/305 |
| 4,969,880 | 11/1990 | Zamierowski | 604/180 |
| 4,985,019 | 1/1991 | Michelson | |
| 5,037,397 | 8/1991 | Kalt et al. | |
| 5,100,396 | 3/1992 | Zamierowski | |

Primary Examiner—C. Fred Rosenbaum
Assistant Examiner—Chalin Smith
Attorney, Agent, or Firm—Litman, McMahon & Brown

[57] ABSTRACT

A fastening system includes a membrane assembly which can comprise a pair of body panels secured together at a seam. The membrane panels can comprise a semi-permeable material. A sheath assembly has a tubular configuration with proximate and distal ends and a sheath passage extending therebetween. The sheath assembly can be fastened to the membrane assembly by adhesively securing the sheath assembly adjacent to its proximate end between the membrane panels at the membrane assembly seam. A sheath-to-tube fastener is provided for fastening the sheath assembly to a tube. A fastening method includes the steps of fastening two panels of a membrane assembly together at a seam, fastening a sheath assembly to the membrane assembly between the panels at the seam, and fastening a tube to the sheath. In one embodiment of the present invention a surgical sponge is fastened to the membranes in fluidic connection with the sheath, which is fastened to a suction tube for drawing blood from a surgical site.

31 Claims, 4 Drawing Sheets

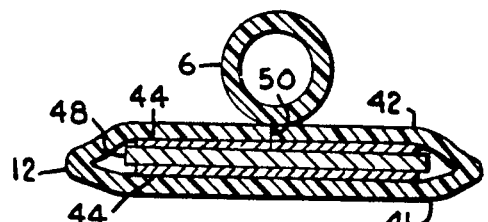
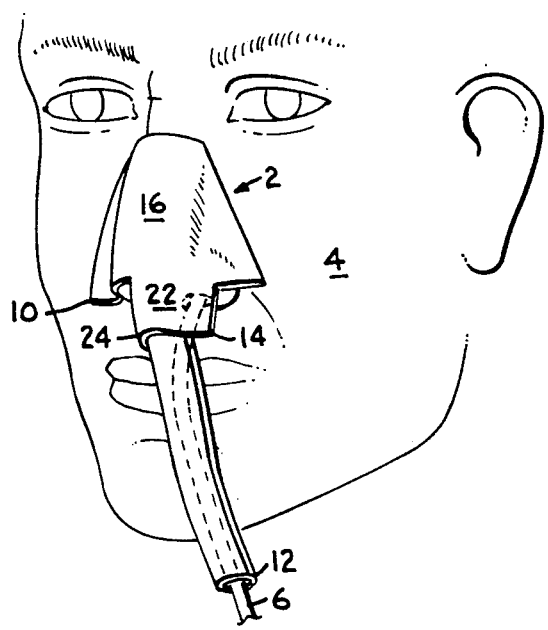
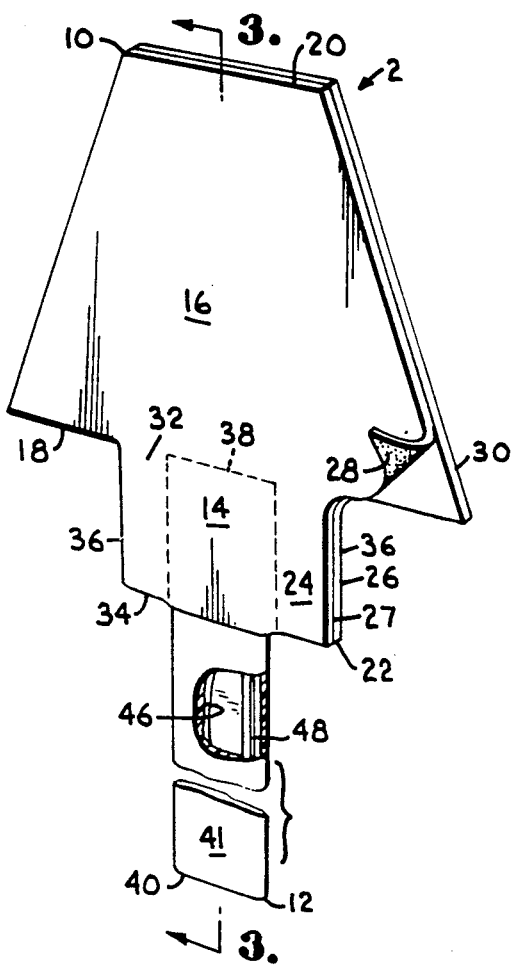
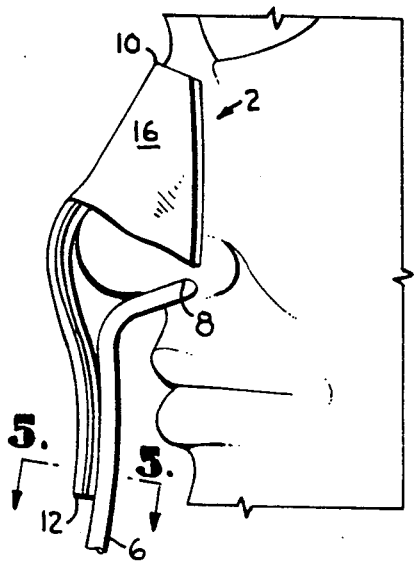
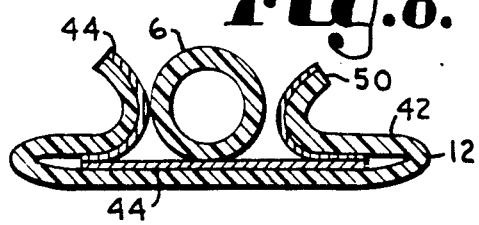
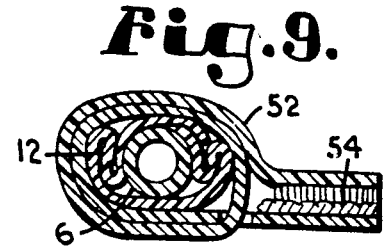

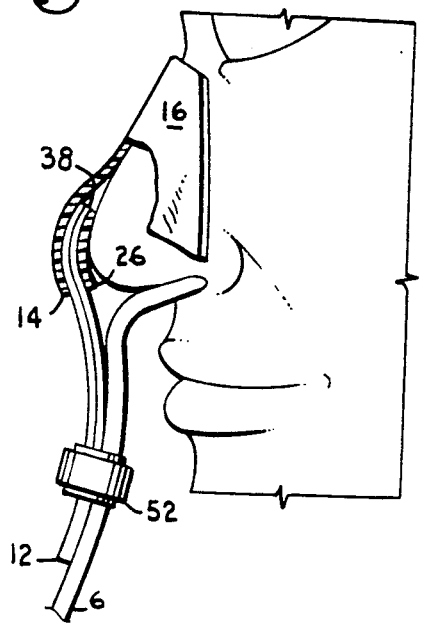
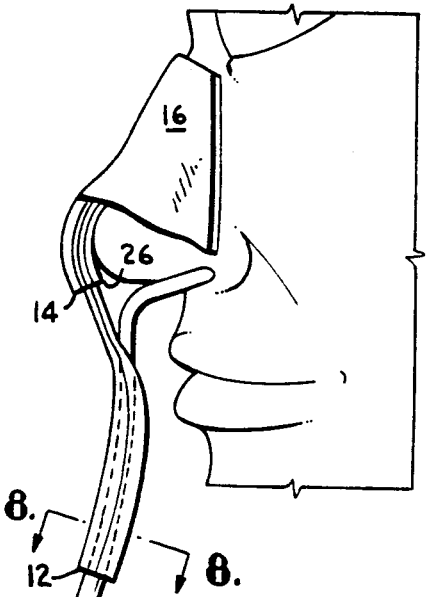
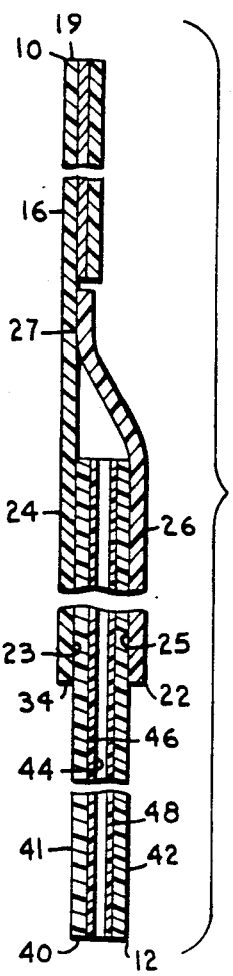
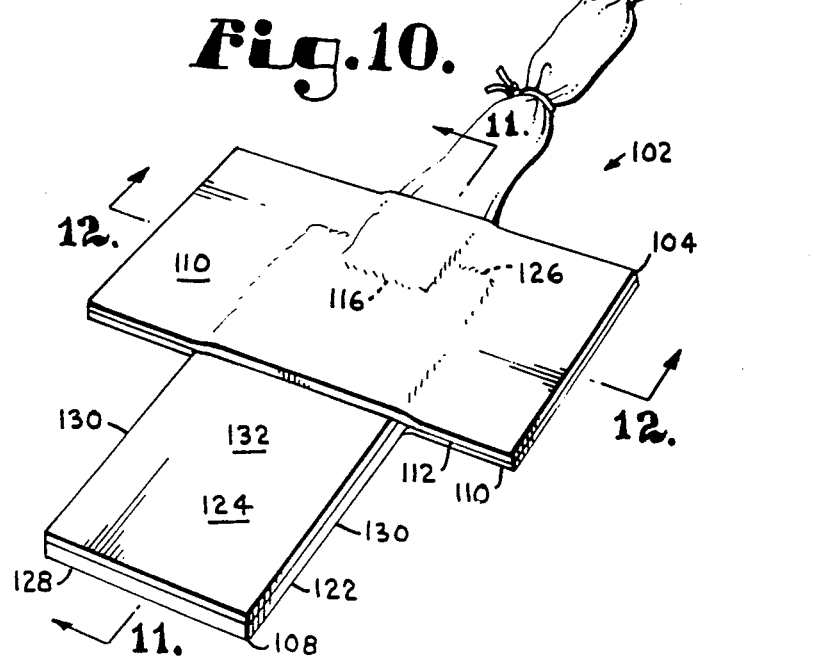

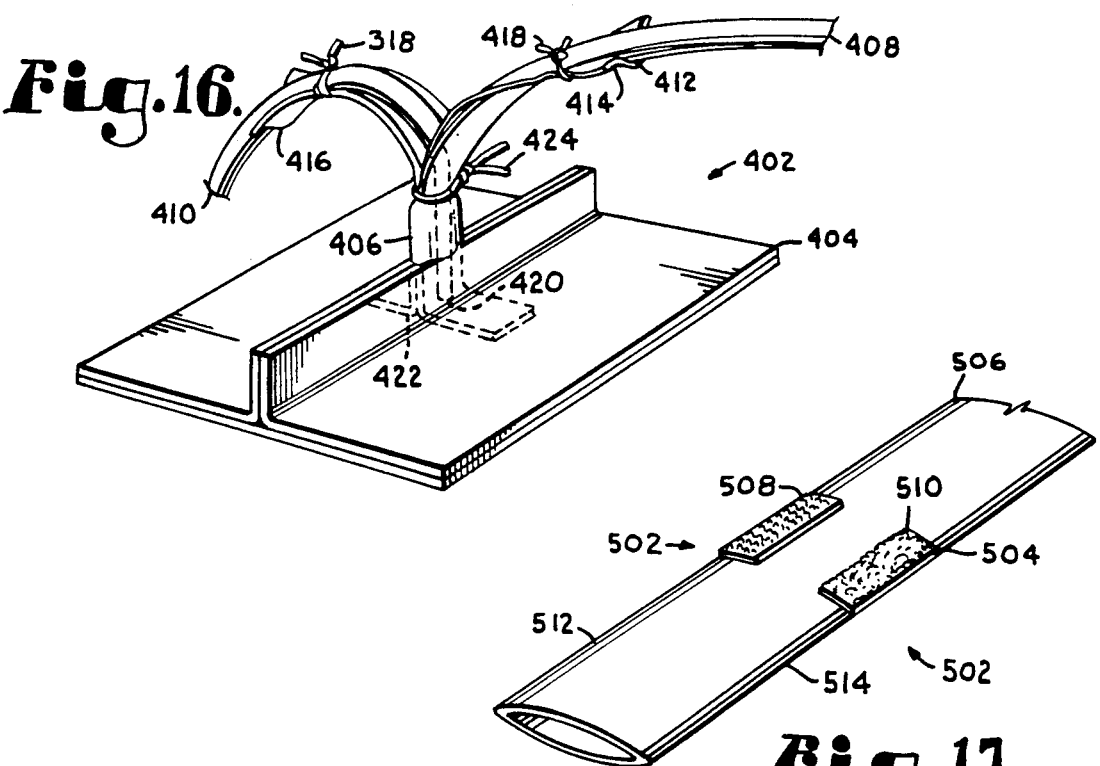
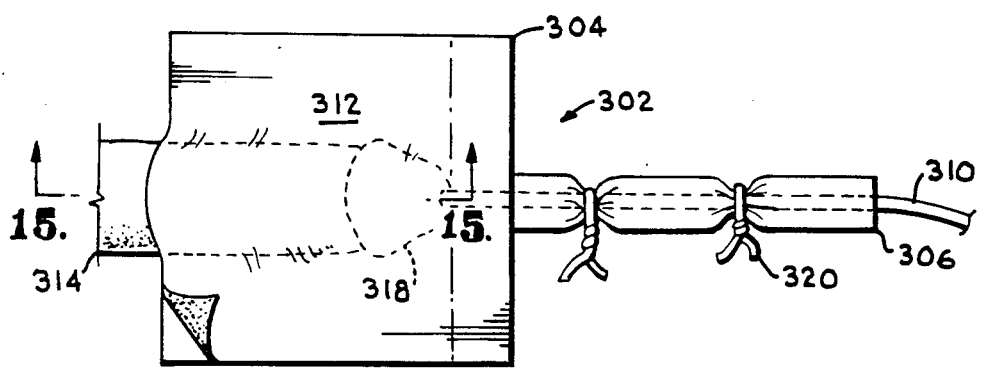
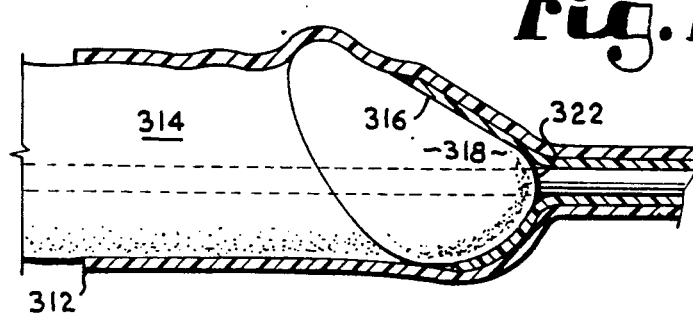

FASTENING SYSTEM AND METHOD

This application is a continuation-in-part of U.S. patent application Ser. No. 504,598, filed Apr. 3, 1990; now U.S. Pat. No. 5,100,396, which is a continuation-in-part of U.S. patent application Ser. No. 07/332,699, filed Apr. 3, 1989, now U.S. Pat. No. 4,969,880.

BACKGROUND OF THE INVENTION

1. Field of the Invention

The present invention relates generally to fastening systems, and in particular to a system and method for fastening tubes to patients.

2. Description of the Related Art

Various fastening systems and methods have heretofore been devised for meeting the requirements of particular applications. For example, in the medical field, a variety of fastening systems are employed in connection with various medical procedures. Previous medical fastening systems include sutures, clamps, belts, ties, adhesive tape and other tapes. Common medical fastening procedures include fastening tubes to patients.

Medical patients are intubated in connection with a number of common medical procedures. For example, nasogastric tubes are inserted into the patient's stomach via a nostril for aspirating the stomach contents. Tubes are commonly inserted through stomal openings, e.g., in connection with ileostomies, gastrostomies, etc.

Intravenous (IV) tubing, catheters, fiber optic cables and electrical wire leads from electrodes all present problems associated with fastening tubes, cables and leads to patients. Frequently, a tube-to-patient connection with some structural integrity is desired, i.e., to reduce the risk of injury from the tube being torn loose from the patient. Since considerable tensile force can be exerted on such tubing (e.g., by an intubated patient rolling over in bed), previous solutions such as secure taping with strong adhesive tape have been utilized with some success. However, there are disadvantages associated with the prolonged application of adhesive tape. Since many types of adhesive tape used for medical applications are relatively impervious, skin covered thereby is susceptible to maceration and the formation of milia consisting of inflamed hair follicles and glands.

Tubes and other flexible lines can also be sutured to patients, but there are disadvantages associated with this technique. For example, the sutures can be uncomfortable to the patient, and can cause infection, inflammation and scaring.

Improved patient comfort can be achieved by applying semi-permeable membranes, which tend to be permeable to vapors, to wound sites. Such membranes are available from several companies, including: "Polyskin" from Kendall Health Care Products Company; "Opsite" from Smith & Nephew, Inc.; "Bioclusive" from Johnson & Johnson Products, Inc.; and "Tegaderm" from 3M Health Care. Such membranes commonly have adhesive faces for adhesion to patient's skin, but are normally relatively thin with little structural integrity. Thus, for all of their patient comfort advantages, the semi-permeable membranes are often not a satisfactory substitute for adhesive tape.

Tapes are also available which have permeable characteristics, but many of them lack sufficient structural integrity for practical use as the sole and exclusive fastening system for tubes and other flexible lines.

However, the semi-permeable membrane materials referred to above can be combined with other, stronger materials, such as flexible plastic tubing, to provide wound dressings with considerable advantages over previous, conventional gauze-and-tape dressings. The Zamierowski U.S. Pat. No. 4,969,880 discloses such a wound dressing which effectively exploits the combined advantages of semi-permeable membranes and flexible plastic tubing.

The applicability of such a combination to a variety of fastening applications is addressed by the present invention.

Another problem commonly encountered in medical surgical procedures relates to the evacuation of blood from the operating site. Devices have been provided for capturing the blood and other fluids, e.g., eye drains available from Merocel Corporation which are fastened to patient's cheeks during ophthalmologic procedures. Sponges and gauze are often used for evacuating blood and other fluids from operating sites. Suction tubes are also utilized, e.g., with cannulae, and can be provided with small sponge attachments on their ends for gathering fluid, e.g. Tebbett's suction pads available from Dow Corning. The present invention can be utilized as a device for fastening and fluidically communicating surgical sponges with suction for the collection of blood and other fluids during surgery, which can reduce the need for handling and weighing blood-saturated sponges in the operating room, which is frequently required at present to determine a volume of blood replacement required for a patient during surgery.

SUMMARY OF THE INVENTION

In the practice of the present invention, a fastening system and method are provided for fastening a variety of tubes to patients for performing various medical procedures thereon. The fastening system can comprise a membrane assembly consisting of a pair of membrane body panels adhesively joined at a seam extending transversely across the membrane assembly. The membrane assembly can comprise a semi-permeable material with an adhesive face covered by an adhesive backing prior to use. A sheath assembly includes proximate and distal ends and a sheath passage extending therebetween. The sheath assembly is fastened to the membrane assembly by extending the sheath assembly between the body panels at the membrane assembly seam in proximity to the sheath assembly proximate end, which can be split to form a pair of sheath proximate end tabs. A sheath-to-tube fastener is provided for fastening the sheath to a tube inserted in the patient. The fastening system can also mount the sheath adjacent to an end edge thereof, for example in a fastening system construction particularly designed for fastening a nasogastric tube to a patient.

A surgical suction fastening system is also disclosed wherein a sponge is sandwiched between the panels of the membrane assembly with a portion of the sponge extending beyond a membrane assembly for drawing fluids, e.g., blood from a surgical site. Methods of fastening the present invention in connection with various medical procedures are further disclosed, particularly those involving intubation of a patient, e.g., nasogastric, suction, intravenous, Foley catheter, stomal and percutaneous tubing.

Another method in the practice of the present invention involves sandwiching a surgical sponge between the membrane assembly panels and fastening the sheath to a suction tube for suction evacuating blood from an operating site.

OBJECTS AND ADVANTAGES OF THE INVENTION

The principle objects and advantages of the present invention include: providing a fastening system and method, providing such a fastening system and method which are particularly well-adapted for medical applications; providing such a system and method for fastening tubing to a medical patient; providing such a system and method for fastening a surgical sponge to a suction source in fluidic communication; providing such a system and method which have considerable structural strength; providing such a system and method which are relatively comfortable to patients; providing such a system and method which can reduce or minimize maceration and the formation of milia as compared to adhesive tape systems and methods; providing such a system and method which allow a wide variety of applications with a common device; providing such a device and method which can help control nosocomial and other infections; and providing such a device and method which are efficient in operation, economical to manufacture and practice, and are particularly well designed for the proposed usages thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a fastening system embodying the present invention, shown fastening a nasogastric tube.

FIG. 2 is an enlarged, perspective view of the fastening system, shown prior to application to a patient.

FIG. 3 is an enlarged, fragmentary, cross-sectional view of the fastening system, taken generally line 3—3 in FIG. 2.

FIG. 4 is a side elevational view of the fastening system.

FIG. 5. is an enlarged cross-sectional view of the fastening system taken generally along line 5—5 in FIG. 4.

FIG. 6 is a side elevational view of the fastening system, showing the nasogastric tube partially within a sheath thereof.

FIG. 7 is an enlarged cross-sectional view of the fastening system, taken generally along line 7—7 in FIG. 6.

FIG. 8 is a side elevational view of the fastening system, particularly showing the nasogastric tube enclosed within the sheath and secured by a cinch loop fastener.

FIG. 9 is an enlarged cross-sectional view of the fastening system taken generally along line 9—9 in FIG. 8.

FIG. 3a is an enlarged, fragmentary, cross-sectional view thereof taken generally along 3a—3a in FIG. 2a.

FIG. 10 is a perspective view of a fastening system for a surgical sponge comprising a second modified or alternative embodiment of the present invention.

FIG. 14 is a plan view of a fastening system comprising a forth modified or alternative embodiment of the present invention, shown attaching a Foley catheter to a patient.

FIG. 15 is an enlarged, fragmentary, cross-sectional view thereof taken generally along line 15—15 in FIG. 14.

FIG. 16 is a perspective view of a fastening system comprising a fifth modified or alterative embodiment of the present invention, showing a pair of tubes attached to the fastening system for connection to a patient.

FIG. 17 is a fragmentary, perspective view of a fastening system comprising a sixth modified or alternative embodiment of the present invention, with a hook-and-loop fastener for fastening a sheath.

DETAILED DESCRIPTION OF THE PREFERRED EMBODIMENTS

I. Introduction and Environment

Figure 12:
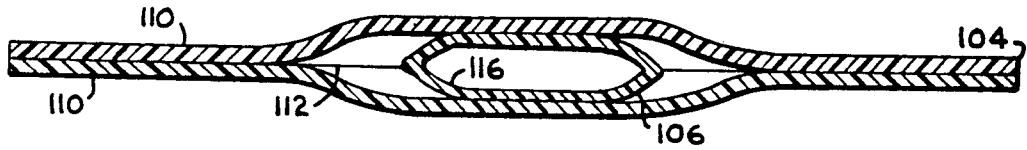
FIG. 12 is an enlarged cross-sectional view thereof taken generally along line 12—12 in FIG. 10.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

II. Nasogastric Tube Fastening System 2

Referring to the drawing in more detail, the reference numeral 2 generally designates a medical fastening system which embodies the present invention. Without limitations on the generality of useful applications of the medical fastening system 2, it is shown applied to a medical patient's face 4 attaching a nasogastric tube 6, which is inserted through a nostril 8 of the patient for aspirating the stomach contents.

The fastening system 2 generally comprises a membrane assembly 10, a sheath assembly 12, and a sheath-to-tube fastener 14.

The membrane assembly 10 includes a first body panel 16 with first and second end edges 18, 19 and opposite side edges 20. A membrane flap or extension 22 extends from the first end edge 18 and includes a first flap panel 24, which can be integral with the body panel 16, and a second flap or body panel 26. The body panel 16 includes an adhesive layer 28 which can be covered by an adhesive backing 30.

The body panel 16 and the flap panels 24, 26 can comprise a vapor-permeable, transparent, polyurethane film material of the type which is available from a number of manufacturers, e.g.: "Tegaderm" dressing from the 3M Company; "Bioclusive" dressing from Johnson & Johnson Products, Inc.; "OpSite" dressing from Smith & Nephew Inc.; and "Polyskin" dressing from Kendall Health Care Products, Inc.

The flap or extension 22 includes a proximate edge 32 connected to the body first end edge, a distal edge 34, opposite side edges 36 and an adhesive seam 27 between adhesive layers 23, 25 on the first and second flap panels 24, 26.

The sheath assembly 12 includes proximate and distal ends 38, 40 with first and second sheath faces 41, 42 each having an adhesive layer 44 thereon adjacent to a sheath passage 46. An adhesive release strip 48 extends through the sheath passage 46. One or both of the sheath faces 41, 42 can be provided with a tear line or marking 50 for access to the passage 46.

A method of fastening the nasogastric tube 6 to a patient is disclosed, and includes the steps of pealing away the adhesive backing 30 and adhesively securing the body panel 16 to the nose and/or cheeks of the patient's face 4 (FIGS. 1 and 4).

The flap or extension 22 comprises a double layer of the semi-permeable membrane material with adhesive layers 28 thereof attached at the seam 27 whereby the flap or extension 22 will not adhere to the patient. The sheath assembly 12 can overlie the tube 6, as shown in FIGS. 1, 4 and 5, and can be temporarily secured thereto with a cinch loop fastener 52 as shown in FIG. 6. The cinch loop fastener 52 can include a hook-and-loop fastener 54 for releasably cinching the sheath assembly 12 to the tube 6. Such a fastener is shown in FIG. 9. However, various other sheath-to-tube fastening means could be employed, including twist ties, rubber bands, clips, etc. By employing a releasable fastener 52, the tube 6 can easily be repositioned with respect to the fastening system 2. The position of the tube 6 can be confirmed by X-ray examination or by other means, and can be adjusted if necessary.

When the tube 6 is properly positioned, it can be resecured to the fastening system 2 by opening the sheath assembly 12 and placing the tube 6 within the sheath passage 46. The sheath assembly 12 can be opened by cutting it longitudinally, or by tearing it along a tear line 50 to provide access to the passage 46. The adhesive release strip 48 can then be removed from the sheath assembly 12 and the tube 6 placed in the passage 46 as shown in FIG. 8. The sheath 12 can then be folded over the tube 6 (FIGS. 7 and 9). The tube 6 can be adhesively secured in place by pressing the adhesive layers 44 of the sheath 12 thereagainst. The tube 6 can also be secured within the sheath 12 by the cinch loop fastener 52 (FIG. 9). With the tube 6 thus secured, the tube is relatively securely attached to the patient. Patient comfort is facilitated by the use of the semi-permeable material for the membrane assembly 10, which passes vapors and air for breathability. Thus, as compared to relatively impervious fastening systems (e.g., adhesive tape), greater patient comfort can be achieved and skin problems such as maceration or formulation of milia (gland or hair follicle inflammation accompanied by pustules) can be reduced. Furthermore, the nasal tip and the nostril rim area of the patient can be observed for evidence of inflammation, infection, etc., and can be promptly detected. Furthermore, necrosis of the nostril tip, which often accompany overly forceful adhesive taping, can be observed and therefore minimized or avoided.

Figure 2A:
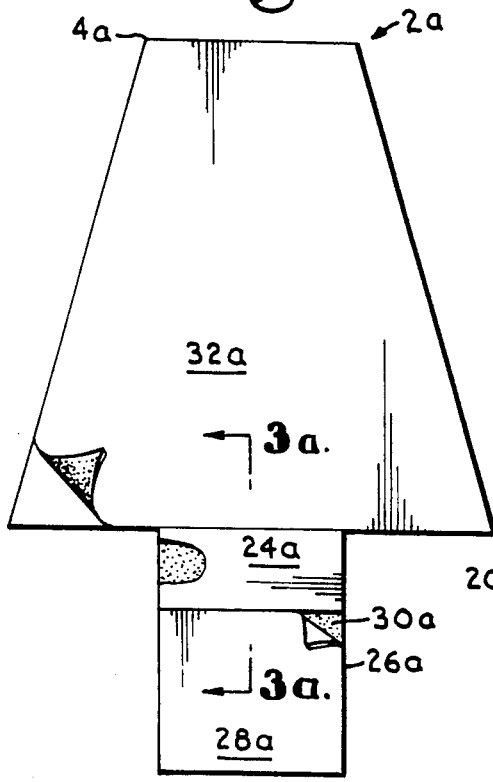
FIG. 2a is a plan view of a fastening system for a nasogastric tube comprising a first modified or alternative embodiment of the present invention.
Figure 3A:
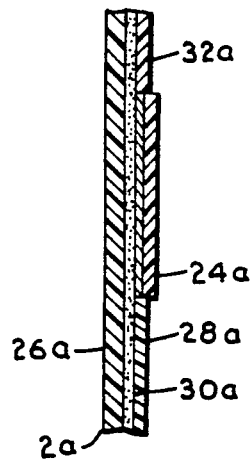

A fastening system 2a comprising a first modified or alternative embodiment of the present invention is shown in FIGS. 2a and 3a. The fastening system 2a is particularly adapted for fastening a nasogastric tube 6, but like the fastening system 2, could also fasten an intravenous tube and other types of tubing and flexible lines. The fastening system 2a includes an intermediate membrane strip 4a adhesively attached to a first flap panel 24a. The first flap panel 24a includes an end portion 26a with adhesive backing layer 28a which can be peeled away for exposing an adhesive layer 30a.

In using the fastening system 2a, a body adhesive backing 32a is peeled away from the membrane 4a to expose the adhesive layer 30a, and the membrane 4a is applied to the patient as described above. The first flap panel 24a is preferably positioned in proximity to the patient's nostrils, and since it does not have any exposed adhesive, the fastening system 2a can be utilized to leave the patient's nostrils clear for breathing. The extension adhesive backing 28a is peeled away to expose the adhesive layer 30a and the membrane end portion 26a can be wrapped around the nasogastric tube 6 for securing same to patient.

III. Suction Fastening System 102

A surgical suction fastening system 102 comprises a second modified or alternative embodiment of the present invention and is shown in FIG. 10. The surgical suction fastening system 102 generally includes a membrane 104, a sheath assembly 106 and a sponge assembly 108. The membrane and sheath assemblies 104, 106 can comprise, for example, a wound dressing as shown in my U.S. Pat. No. 5,100,396 for fluidic connection system and method, which is co-pending herewith and which is incorporated herein by reference, along with my U.S. Pat. No. 4,969,880.

The membrane assembly 104 comprises a pair of semi-permeable panels 110 which are adhesively joined at a membrane assembly seam 112 whereat a proximate end 114 of the sheath assembly 106 is secured in position. The sheath proximate end 114 forms a split mouth 116 with first and second mouth tabs 118, 120 each positioned adjacent to a respective membrane assembly panel 110.

Figure 11:
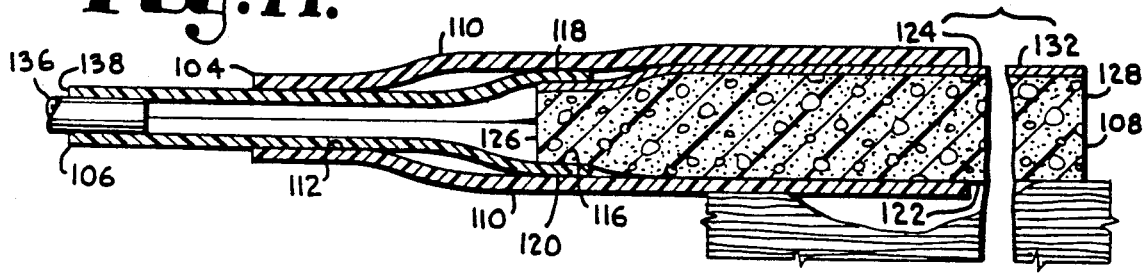
FIG. 11 is an enlarged, fragmentary, cross-sectional view thereof, taken generally along line 11—11 in FIG. 10.

The sponge 108 includes a first or open face 122 and a second or occluded face 124, proximate and distal ends 126, 128 and opposite side edges 130. A sponge backing material or layer 132 which can cover the second or occluded face 124 of the sponge 108 and can be relatively impervious. As shown in FIG. 11, the sheath split mouth 116 is adapted to receive a portion of the sponge 108 between the mouth tabs 118, 120 adjacent to the sponge proximate end 126.

In operation, the fastening system 102 can be used singly or in multiples to draw blood from an open dissection plane, particularly for the purpose of maintaining a critical point free of blood. The sheath assembly 106 can be attached, e.g., by twist ties 134, to a suction line 136 in an area between a distal end 138 of the sheath assembly 106 and the membrane assembly seam 112. The suction tube 136 can be attached to a suitable suction source (not shown). The membrane assembly 104 can comprise either impervious (e.g., thin, flexible) or semi-permeable material. Exposure to and immersion in blood and other fluids may cause a semi-permeable material to become less permeable, with a corresponding enhancement of the suction capabilities of the system 102.

As described in my above-referenced U.S. Pat. No. 4,969,880, such a dressing may also be applied over a variety of surface wounds, including burns, cuts, scrapes and ulcers of various types, e.g. diabetic, decubitus, peripheral vascular disease, venous stasis and trauma ulcers. In use, such a dressing promotes the evacuation of drained fluids (and hence promotes removal of toxins and bacteria from the wound), protects against infection, promotes healing, and is particularly well adapted for the protection and regeneration of skin graft donor sites.

In an evacuation mode of operation such as might be desirable for forty-eight hours or so after removal of a split-thickness skin graft at a donor site, fluid can be actively evacuated through the tube 136. Such active evacuation is achieved by attaching the tube 136 to a suction/vacuum source whereby the fluid is positively drawn from the wound site. The suction/vacuum source may comprise a motorized pump operated as necessary to achieve the treatment objectives.

The membrane, sheath and sponge assemblies 104, 106, 108 can be manufactured or preassembled in various configurations. Alternatively, the fastening system 102 can be assembled by the health care practitioner by placing a suitable sponge assembly 108 in a premanufactured membrane assembly 104 and sheath assembly 106, which could be similar to my fluidic connection system disclosed in my U.S. Pat. No. 5,100,396 referred to above. Preferably the material comprising the sponge 108 is resistant to shredding and strong enough to not break apart or disintegrate in the wound or operating site. The sponge 108 could be threaded with a radioopaque thread (e.g., where the membrane assembly panels 110 are joined to the sponge 108 in a middle area thereof) to provide greater structural integrity and also to facilitate detection by X-ray if the sponge were lost in the wound. By providing transparent, or at least translucent, membrane assembly panels 110 and a sheath assembly 106, the movement of blood through the system 102 can be observed. Furthermore, an anti-clotting coating can be provided on the sponge 108 to facilitate efficiency. It is anticipated that most of the blood and fluid would enter the sponge 108 through the exposed area of the first or open face 122 of the sponge 108 through the exposed portions of the sponge side edges 130, and through the sponge distal end 128. However, the sponge 108 could be provided without a backing material or layer 132 for suction through its second face 124.

The sheath assembly 106 preferably is relatively flexible for mobility of the fastening system 102. The sheath assembly 106 can be prevented from collapsing under the suction force by providing it with permanent, crimped edges. Foldable, flat sheathing is available from Aero International, Inc. of Reading, Pa. Alternatively, the sheath assembly 106 can have longitudinal ridges for providing resistance to collapse. The sheath assembly 106 can have a length of about eighteen inches to twenty-six inches for many uses, but its length is practically unlimited. Various connector devices can be used for attachment to the sheath assembly 106, such as a male adapter, which is sometime referred to as a "Christmas tree" for insertions in standard suction tubing, or a "suction block" for allowing multiple fastening systems 102 to be connected to a common suction source. Rubber bands, O-rings, tape and other fastening systems can be used for the sheath-to-tube fastening means. Suction devices such as those commonly used in tonsillectomies can be employed. The blood and fluid connected through the fastening system 102 can be collected remote from the patient for measurement to determine how much, if any, fluid is to be replaced in the patient.

IV. Intravenous Tube Fastening System 202

Figure 13:
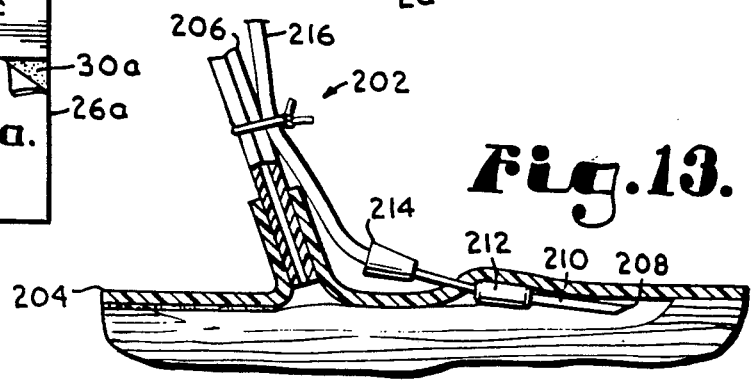
FIG. 13 is a cross-sectional view of a fastening system comprising a third modified or alternative embodiment of the present invention, shown fastening an intravenous tube to a patient.

An intravenous ("IV") tube fastening system 202 comprising a third modified or alternative embodiment of the present invention is shown in FIG. 13. A membrane assembly 204 and a sheath assembly 206 can be substantially the same as the membrane and sheath assemblies 104, 106 described above in connection with the surgical suction fastening system 102.

The IV tube fastening system 202 can be applied over an IV site or a cannula 208 inserted into the vein of the patient through a skin puncture site 210. The cannula 108 can be fitted at its distal end with a heparin lock 12 which can lie adjacent to the skin surface.

By forming the membrane assembly 204 of a transparent or translucent material, the heparin lock 212 can be observed through the membrane assembly 204 which overlies it. A hypodermic needle 214 can be inserted through the membrane assembly 204 and into the heparin lock for fluidically connecting an IV tube 216 connected to the needle 214 with the cannula 208 whereby an intravenous flow of fluid can be established. The IV tube 216 can be secured to the sheath assembly 206 by any suitable means including those discussed above. By effectively utilizing the strength, adhesive and vapor permeability properties of the membrane assembly 204 and the sheath assembly 206, the IV puncture site 210 can be effectively closed off against bacteria to reduce the risk of infection, and the IV tube 216 can be effectively secured to the patient to minimize the risk of being inadvertently pulled loose. The semi-permeable nature of the membrane assembly 204 can facilitate patient comfort, particularly if the IV system is left in place for a prolonged period of time. The transparent or translucent nature of the membrane assembly 204 facilitates observation of the puncture site 210, whereby inflation or infection can be promptly detected and treated.

V. Foley Catheter Fastening System 302

A Foley catheter fastening system 302 comprising a fourth modified or alternative embodiment of the present invention is shown in FIGS. 14 and 15, and generally comprises a membrane assembly 304 and a sheath assembly 306, which can be generally similar to the membrane and sheath assemblies described above in connection with the fastening systems 102 and 202.

In the application of the fastening system 302 to a patient, a Foley catheter 308 is applied to the patient by inserting a catheter tube 310 thereof through the urethra and into the bladder of the patient. The tube 310 mounts a balloon on the end thereof which can be inflated with air or liquid in the patient's bladder. The fastening system can be applied by slipping the sheath 306 over the catheter tube 310 and adhesively securing panels 312 of the membrane assembly 304 to the patient's penis 314. Sheath end tabs 316 can be placed on top of and below the glans or penile head 318.

The sheath 306 can be secured to the tube 310 by suitable sheath-to-tube fasteners 320, which can be of any of the types discussed above. The membrane assembly 304 in conjunction with the sheath assembly 306, would enclose the meatal/catheter junction 322 and could be helpful in controlling nosocomial infection entering the urethra through this junction.

Due to the transparent or translucent nature of the membrane assembly 304, the catheter tube 310 can alternatively be inserted after the fastening system 302 is in place by sliding it through the sheath assembly 306 and then into the urethra.

VI. Multiple Tube Fastening System 402

A multiple tube fastening system 402 comprising a fifth modified or alternative embodiment of the present invention is shown FIG. 16 and generally comprises a membrane assembly 404 and a sheath assembly 406, which can be substantially similar to the membrane and sheath assemblies described above in connection with fastening systems 102, 202 and 302. A percutaneous tube 408 and a suction tube 410 extend into the sheath assembly 406 in juxtaposed relation. The sheath assembly 406 can be longitudinally, axially split from a distal end 412 of the sheath assembly 406 to a location in spaced relation from the membrane assembly 404, whereby first and second sheath half-sections 414, 416 are formed. The first sheath half-section 414 can be attached to the percutaneous tube 408 by suitable fastening means 418, and the second sheath half-section 416 can be fastened to the suction tube 410 by similar fastening means 318.

The fastening system 402 can be used in conjunction with a gastrostomy or antrostomy tube 408, with the suction tube 410 provided for draining fluid leakage from around the stomal site. The suction tube 410 can terminate at a proximate end 420 in proximity to a proximate end 422 of the sheath assembly 406. A relatively fluid-tight connection can be formed between the sheath assembly 406 and the tubes 408, 410 with a sheath-to-tube fastening means 424, or adhesive on the inside of the sheath assembly 406, or a combination of both. In this manner irrigation and suction can be applied simultaneously or consecutively without having to remove or disturb the fastening system 402.

Without limitation on the generality of useful applications of the fastening system 402, it is applicable to other surgical procedures such as ileostomy and the placement of ileo conduits, and virtually any other stomal procedures.

Alternatively, the fastening system 402 can include a sheath assembly in the form of a Y-connector or T-connector with supply sources of liquid connected to one branch of the connector and suction sources connected to the branch. Still further, multiple sheath assemblies 406 can be connected to the membrane assembly 404. Tubing and other flexible lines for multiple functions can also be achieved with the fastening system 402 by providing tubing with multiple lumens. Such flexible lines can comprise tubing, electrical wires, e.g., connected to electrodes, fiber optic cables, etc.

IV. Fastening System 502 with Integral Sheath Attachment

A fastening system 502 with an integral sheath clamp 504 is shown in FIG. 17 and comprises a sixth modified or alternative embodiment of the present invention. The fastening system 502 includes a sheath assembly 506 which can otherwise be substantially similar to the sheath assemblies 106, 206, 306 and 406 described above. The integral sheath clamp 504 comprises first and second fastening patches 508, 510 secured to the sheath assembly 506 in proximity to respective opposite second side edges 512, 514 of the sheath assembly 506. The fastening patches 508, 510 can comprise, for example, the hook and loop components of a hook-and-loop fastening system, such as that available under the trademark "VELCRO". Alternatively, the fastening system 502 can comprise other types of mechanical fasteners, such as snaps, etc., or adhesive fasteners. The sheath clamp 504 is particularly useful for temporarily securing a tube to the sheath assembly 506, or as in the step shown in FIG. 6 for temporarily securing a nasogastric tube 6. By including the sheath clamp 504 in the sheath assembly 506, convenience in use can be facilitated because the health care provider does not need to locate a clamping device, which might otherwise be subject to becoming lost or misplaced.

It is to be understood that while certain forms of the present invention have been illustrated and described herein, it is not to be limited to the specific forms or arrangement or parts described and shown.

What is claimed and desired to be secured by letters patent is as follows:

1. A fastening system for fastening an elongated tube proximate to a skin surface, which system comprises:
   (a) a membrane assembly including at least one membrane panel having an adhesive face;
   (b) a sheath assembly having a generally tubular configuration, proximate and distal ends, and a sheath passage extending between said sheath ends, said sheath assembly comprising a flexible material;
   (c) membrane-to-sheath fastening means for fastening said membrane assembly directly to said sheath assembly; and
   (d) sheath-to-tube fastening means for fastening said sheath assembly to said tube with said tube at least partially inserted within said sheath passage.

2. The invention of claim 1 wherein:
   (a) said membrane assembly includes first and second membrane panels each having an adhesive face, said membrane assembly having a seam whereat said panels are adhesively joined together at their respective adhesive faces.

3. The invention of claim 2, which includes:
   (a) said membrane-to-sheath fastening means comprising said sheath assembly being adhesively secured within said membrane assembly seam.

4. The invention of claim 2, which includes:
   (a) said first membrane panel including first and second end edges and a pair of opposite side edges;
   (b) said first membrane panel further including a first flap panel extending from the first end edge thereof;
   (c) said second membrane panel comprising a second flap panel adhesively secured to said first flap panel at the seam; and
   (d) said first and second flap panels forming a membrane assembly extension.

5. The invention of claim 1, which includes:
(a) an adhesive layer on said sheath assembly within said sheath passage.

6. The invention of claim 5, which includes:
(a) a sheath adhesive backing strip extending through said sheath passage in releasable engagement with said sheath adhesive layer.

7. The invention of claim 1 wherein:
(a) said sheath-to-line fastening means comprises a cinch belt with a hook-and-loop fastener.

8. The invention of claim 1 wherein:
(a) said sheath-to-tube fastening means comprises a twist tie.

9. The invention of claim 1 wherein:
(a) said sheath-to-line fastening means comprises a hook-and-loop fastener mounted on said sheath, with hook and loop portions thereof positioned in spaced relation on said sheath.

10. The invention of claim 3 wherein:
(a) said sheath assembly is secured in said membrane assembly seam in proximity to said sheath assembly proximate end; and
(b) said sheath assembly includes a split mouth at its proximate end with a pair of tabs each connected to a respective membrane assembly panel.

11. A system for fastening a sponge to a suction tube, said sponge including two opposite ends, two opposite sides, and a top and a bottom face, said system comprising:
(a) a membrane assembly including at least one body panel having an adhesive face, first and second end edges and opposite side edges;
(b) said body panel comprising a flexible material;
(c) a flexible sheath assembly having a generally tubular configuration with proximate and distal ends and a sheath passage extending therebetween, said sheath assembly having a split, open mouth at its proximate end with first and second sheath mouth tabs, said mouth tabs being directly fastened to said membrane assembly in proximity to said sheath assembly proximate end;
(d) sponge fastening means for fastening said sponge to said body panel with a portion thereof between said sheath mouth tabs; and
(e) sheath-to-tube fastening means for fastening the sheath to a suction tube.

12. The invention of claim 11 wherein:
(a) said sponge is positioned with a portion protruding past said membrane assembly to expose a portion of said top and/or bottom faces; and
(b) said surgical sponge includes a backing layer with less permeability than a remaining portion of said sponge, said backing layer at least partially covering the exposed portion of said top or bottom face of said sponge.

13. The invention of claim 11 wherein:
(a) said membrane assembly includes first and second membrane panels each having an adhesive face, said membrane assembly having a seam whereat said panels are adhesively joined together at their respective adhesive faces; and
(b) said mouth tabs are fastened within said membrane assembly seam.

14. A system for fastening a pair of elongated tubes proximate to a patients skin, which comprises:
(a) a membrane assembly including at least one membrane panel having an adhesive face, first and second end edges and opposite side edges;
(b) a sheath assembly having a generally tubular configuration, proximate and distal ends, and at least one sheath passage extending between said sheath ends, said sheath assembly comprising a flexible material;
(c) said sheath assembly being secured directly to said membrane assembly in proximity to said sheath assembly proximate end; and
(d) first and second sheath-to-tube fastening means each adapted for fastening a respective tube to said sheath assembly with at least one of said tubes at least partially inserted within said sheath passage.

15. The invention of claim 14 which includes:
(a) said sheath assembly being split adjacent to its distal end and including first and second sheath half sections; and
(b) each said tube being fastened to a respective sheath half section.

16. The invention of claim 14 wherein:
(a) said sheath assembly includes first and second branches each fastened to a respective tube.

17. The invention of claim 16 wherein:
(a) said sheath assembly first and second branches are interconnected by a T-connector.

18. The invention of claim 16 wherein:
(a) said sheath assembly first and second branches are interconnected by a Y-connector.

19. The invention of claim 14, which includes:
(a) a second sheath assembly having a generally tubular configuration, proximate and distal ends and a sheath passage extending between said sheath ends, said second sheath assembly comprising a flexible material;
(b) said second sheath material being secured directly to said membrane assembly in proximity to said second sheath assembly proximate end; and
(c) said second tube being fastened to said second sheath assembly.

20. The system of claim 14 wherein:
(a) said membrane assembly includes first and second membrane panels each having an adhesive face, said membrane assembly having a seam whereat said panels are adhesively joined together at their respective adhesive faces.

21. A method of fastening a flexible tube proximate to a patient's skin, which comprises the steps of:
(a) providing a membrane assembly including at least one membrane panel having first and second end edges, opposite side edges and an adhesive face;
(b) providing a sheath with a generally tubular configuration and proximate and distal ends with a sheath passage extending therebetween, said sheath assembly comprising a flexible material;
(c) adhesively securing the sheath directly to the membrane assembly;
(d) fastening said membrane panel at its adhesive face to the patient; and
(e) fastening the tube to the sheath, with said tube at least partially inserted within said sheath passage.

22. The invention of claim 21 wherein said tube comprises a nasogastric tube and which includes the additional steps of:
(a) releasing said tube from said sheath;
(b) repositioning said tube with respect to said patient; and
(c) reattaching said sheath to said tube.

23. The invention of claim 21 wherein said tube comprises an intravenous tube, and which includes the additional steps of:
(a) inserting a cannula into the patient at a puncture site;
(b) providing a heparin lock on said cannula;
(c) covering said puncture site and said cannula with said membrane assembly;
(d) inserting a hypodermic needle through said membrane assembly and into said heparin lock; and
(e) connecting said hypodermic needle to said intravenous tube.

24. The invention of claim 21 wherein said tube comprises part of a Foley catheter, and which includes the additional steps of:
(a) inserting the Foley catheter into the urethra of a patient;
(b) placing the membrane assembly over the urethra/catheter junction; and
(c) inserting the catheter tube through the sheath.

25. The invention of claim 23 wherein a second tube is connected to the patient, and which includes the additional steps of:
(a) providing a second sheath assembly;
(b) connecting said second sheath assembly to said membrane assembly; and
(c) connecting said second tube to said second sheath assembly.

26. The method of claim 21 wherein:
(a) said providing a membrane assembly step includes
 (i) providing first and second membrane panels each having an adhesive face; and
 (ii) adhesively joining said panels together at their respective adhesive faces to provide a seam.

27. The method of claim 26 wherein:
(a) said adhesively securing step includes
 (i) adhesively securing the sheath within the membrane assembly seam.

28. A method of fastening a sponge with first and second faces to a suction tube, which comprises the steps of:
(a) providing a membrane assembly with at least one membrane panel having first and second end edges, opposite side edges and an adhesive face;
(b) providing a flexible sheath assembly with a generally tubular configuration, proximate and distal ends and a passage extending therebetween;
(c) fastening said sheath assembly directly to said membrane assembly in proximity to said sheath assembly proximate end;
(d) placing at least a portion of said sponge adjacent said membrane assembly;
(e) adhesively securing said membrane assembly panel to said sponge with said sponge fluidically communicating with said sheath; and
(f) placing said suction tube at least partially within said sheath passage and attaching said 29. The invention of claim 28, which includes the additional steps of:
(a) attaching said sponge to said membrane assembly in an orientation such that said sponge protrudes past said membrane assembly to expose a portion of said faces; and
(b) providing said sponge with a layer having less permeability than a remainder of said sponge, said less permeable layer at least partially covering the exposed portion of said first or said second face.

30. The invention of claim 28 wherein:
(a) said providing a membrane assembly step includes
 (i) providing first and second membrane panels each having an adhesive face; and
 (ii) adhesively joining said panels together at their respective adhesive faces to from a seam.

31. The method of claim 30 wherein:
(a) said adhesively securing step includes
 (i) adhesively securing the sheath within the membrane assembly seam.

* * * * *